US00PP19891P3

(12) United States Plant Patent
Thome

(10) Patent No.: US PP19,891 P3
(45) Date of Patent: Apr. 7, 2009

(54) APPLE TREE NAMED 'B. THOME MCINTOSH'

(50) Latin Name: *Malus domestica*
Varietal Denomination: B. Thome McIntosh

(76) Inventor: Bernard J. Thome, 1660 Eight Mile Rd., Comstock Park, MI (US) 49321

( * ) Notice: Subject to any disclaimer, the term of this patent is extended or adjusted under 35 U.S.C. 154(b) by 0 days.

(21) Appl. No.: 11/582,898

(22) Filed: Oct. 19, 2006

(65) Prior Publication Data

US 2008/0134377 P1 Jun. 5, 2008

(51) Int. Cl.
*A01H 5/00* (2006.01)

(52) U.S. Cl. ..... Plt./165
(58) Field of Classification Search ..... Plt./165
See application file for complete search history.

(56) References Cited

U.S. PATENT DOCUMENTS

| | | | | | |
|---|---|---|---|---|---|
| PP4,383 | P | * | 2/1979 | Dewar | Plt./165 |
| PP5,568 | P | * | 10/1985 | Duffett | Plt./290 |
| PP7,002 | P | * | 8/1989 | Greiner | Plt./165 |
| PP7,167 | P | * | 2/1990 | Starling et al. | Plt./165 |
| PP10,770 | P | * | 2/1999 | Hartenhof | Plt./165 |
| PP12,863 | P2 | * | 8/2002 | Crooke | Plt./165 |
| PP12,900 | P2 | * | 9/2002 | Bull et al. | Plt./165 |

* cited by examiner

*Primary Examiner*—Wendy C. Haas

(57) ABSTRACT

A new and distinct variety of McIntosh apple tree, 'Apple Tree named B. Thome McIntosh,' originating as a limb mutation of the *Malus domestica* variety of 'Starling' (U.S. Plant Pat. No. 7,167). This new variety is unique from its parent and other McIntosh cultivars in the greenish coloration of its flesh and the red coloration of the blossom and the leaf petiole.

3 Drawing Sheets

DESCRIPTION OF RELATED APPLICATIONS

The new variety, 'B. Thome McIntosh' differs from its parent and other McIntosh varieties in the following characteristics:

A. The fruit of the new variety ripens with its parent, 'Starling' (U.S. Plant Pat. No. 7,167) and 'Bull' (U.S. Plant Pat. No. 12,900). It ripens 10 to 15 days ahead of 'Pioneer Mac' (U.S. Plant Pat. No. 7,002), 'Hartenmac NS 219' (U.S. Plant Pat. No. 10,770), 'Chick' (U.S. Plant Pat. No. 5,508) and 'Dewar' (U.S. Plant Pat. No. 4,383). It ripens 4 to 6 weeks ahead of 'Miriela' (U.S. Plant Pat. No. 12,863).

B. The new variety differs from its parent, 'Starling' (U.S. Plant Pat. No. 7,167) and 'Bull' (U.S. Plant Pat. No. 12,900) in the color of its flesh and the red coloration of the blossom and the leaf petiole.

Latin name of the genus and species of the plant claimed: *Malus domestica.*

Variety denomination: 'B. Thome McIntosh.'

BACKGROUND OF THE INVENTION

A new and distinct variety of McIntosh apple tree originating as a limb mutation of the *Malus domestica* variety of 'Starling' (U.S. Plant Pat. No. 7,167), hereinafter referred to as the 'B. Thome McIntosh'. This new sport is unique from its parent because the fruit starts coloring 80 days earlier as a full red blush. The color finishes to a virtually 100% solid, bright red blush with flesh that is slightly greener than the parent and with a leaf petiole and blossom with prominent red coloration.

SUMMARY OF THE INVENTION

This new and distinct variety of McIntosh apple tree was discovered in 1999 as a limb mutation of 'Starling' (U.S. Plant Pat. No. 7,167), in an orchard planted in 1985 near Comstock Park, Mich. The new variety was noticed because the fruit started coloring the in mid June, 6 to 8 weeks ahead of all other 'Starling' (U.S. Plant Pat. No. 7,167) fruit in the orchard.

Observations during the next two seasons confirmed the that the fruit colored with a solid, bright red blush with no striping as opposed to 'Starling' (U.S. Plant Pat. No. 7,167), which colors with a distinct stripe. The mature fruit of the new variety finishes to a 100% solid, intense bright red color. The new variety also exhibits a prominent red coloration of the petiole and the blossom.

In August of 2000, buds were taken from the original limb and 100 trees for further testing were produced by cleft grafting onto existing apple trees. In 2001, buds were taken from the original limb and reproduced by chip budding into 116 trees on M9 (NIC 29) rootstock in Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained in Comstock Park, Kent County, Mich., 49345.

FIG. 1 illustrates the fruits and foliage of the new variety at maturity.

FIG. 2 illustrates a section of the fruit and the foliage of the new variety.

FIG. 3 illustrates blossoms of the new variety.

DETAILED BOTANICAL DESCRIPTION

A detailed description of the 'B. Thome McIntosh' cultivar follows using the Royal Horticultural Society of London Colour Chart, 1986 edition, for color identification except where general color terms are sufficient.

Parentage: A limb mutation of 'Starling', (U.S. Plant Pat. No. 7,167). Locality of the original discovery and observations is 1600 Eight Mile Road, Comstock Park, Mich. 49321.

Tree:
- *Age.*—4 years.
- *Size.*—Large, height 2.5 m, width 1 m.
- *Vigor.*—Vigorous, yearly growth averages 1 m.
- *Density.*—Medium.
- *Form.*—Upright, spreading.
- *Production.*—Very productive, averaging 800 bushels per acre.
- *Growth type.*—Non-spur.
- *Bearing.*—Annual.

Trunk:
- *Size.*—13 cm in diameter at 90 cm above ground level.
- *Surface.*—Smooth.
- *Bark color.*—Grey Group 201 B.
- *Lenticels.*—Length 1.5 cm, width 0.5 cm.
- *Lenticel color.*—Grayed White 156 D.
- *Lenticel density.*—2 per $cm^2$.

Branches:
- 3 *year old branch.*—25 mm in diameter, color Grayed Orange 175 A, angle to trunk 30° to 45°.
- 2 *year old branch.*—8 to 10 mm in diameter, length 25 to 25 cm, color Grayed Orange 175 A, angle to $3^{rd}$ year branch 30° to 50°.
- 1 *year old branch.*—5 to 8 mm in diameter, length 30 to 40 cm, color Grayed Purple 187 A; lenticels 0.1 mm in diameter, round, color Grayed Yellow 161 A, angle to $2^{nd}$ year branch 30° to 50°.

Leaves:
- *Size.*—Length 95 mm, width 60 mm.
- *Texture.*—Leathery, crisp.
- *Form.*—Broadly ovate.
- *Base.*—Bluntly pointed.
- *Apex.*—Rounded.
- *Adaxial surface pubescence.*—None.
- *Abaxial pubescence.*—Very fine.
- *Adaxial surface color.*—Yellow Green 147 A.
- *Abaxial surface color.*—Yellow Green 147 C.
- *Venation.*—Pinnate, 10–12 veins, mainly alternate, color Yellow Green 147 C with Grayed Purple 185 B toward mid-vein.
- *Mid-vein.*—Strong coloration of Grayed Purple 185 B extending from base of leaf to within 10 mm of leaf tip.
- *Margin.*—Serrate.
- *Leaf glands.*—Absent.
- *Petiole length.*—33 mm.
- *Petiole width.*—2 mm.
- *Petiole abaxial color.*—Grayed Purple 185 B to Grayed Purple 187 A toward base and abscission layer.
- *Petiole groove.*—None observed.
- *Stipules.*—Very fine, at the base of the petiole on almost all leaves
- *Stipule length.*—7 mm.
- *Stipule width.*—1.5 mm.
- *Stipule color.*—Yellow Green 147 C.

Leaf buds:
- *Length.*—5 mm.
- *Width.*—4 mm.
- *Color.*—Grayed Purple 187 A.
- *Placement on branch.*—Tightly applied to the branch.
- *Internode distance.*—35 mm.

Spurs: present on $2^{nd}$ year and older wood.
- *Length.*—12 to 15 mm.
- *Width.*—6 to 8 mm.
- *Color.*—Grayed Purple 187 A.

Bloom period: early season bloom, approximately April 12 to 19 in Comstock Park, Mich.

Presentation: very showy.

Fragrance: very fragrant.

Fertility: fertile, will pollinate other early blooming varieties such as Idared or Spartan.

Pollination Requirements: requires pollen from other early blooming, fertile varieties such as Spartan (an unpatented selection), Idared (an unpatented selection) or Manchurian Crabapple (an unpatented selection).

Pollen: abundant.

Flowers at Popcorn Stage:
- *Pedicle.*—Length 18 to 22 mm, diameter 2 mm.
- *Pedicel color.*—Green 138 B.
- *Bud.*—Length 9 mm, width 7 to 8 mm.
- *Bud color.*—White 155 D with a blush of Purple Violet 80 D and banding of Purple Violet 80 D on the outer edges of the petals.

Flowers at full bloom:
- *Corolla diameter.*—45 to 55 mm when fully open.
- *Numbers of flowers per cluster.*—3 to 5.
- *Petals.*—Arrangement: generally overlapping. Color: White 155 D with a distinct banding on the outer edges of Purple Violet 80 D on both upper and lower surfaces. Petal Veins: White 155 D on 50% of petals, remaining petals showing distinct vein coloration of Purple Violet 80 D extending from the base of the petal to the outer edges, merging into the banding of Purple Violet 80 D. Shape: broadly ovate, base rounded to abruptly cuneate at junction with receptacle, apex very rounded. Entire petal is cupped with basin 5 mm deep basin from the edge to the center of the petal. Margin: somewhat ruffled with occasional notching at the apex. Size: length 23 to 25 mm, width 18 to 20 mm. Texture: firm.
- *Pedicel.*—Length 25 to 27 mm, width 2 mm, color Green 138 B
- *Sepals.*—5 in number, wedge shaped, sharply pointed, length 5 mm, width 5 mm, color Green 138 B.
- *Filaments.*—Length 8 to 10 mm, width 0.3 mm, color Purple Violet 80 C at base blending to White 155 D at junction with anther.
- *Anthers.*—Length 2 mm, width 1 mm, color Grayed Orange 166 D.
- *Pistil.*—Held slightly lower than anthers in a majority of blossoms.
- *Ovary.*—Length, 4 mm, width 1.5 mm, pubescent, color Green White 157 D.
- *Stigma.*—Width 1 mm, pubescent, color Green White 157 D.
- *Style.*—Length 3 mm, width 1 mm, color Green White 157 D.

Fruit:

*Maturity when described.*—Firm ripe.

*Date of picking.*—September 1, in Comstock Park, Kent County, Mich. generally harvested in one picking.

*Size.*—Axial diameter 80 to 90 mm, transverse diameter 80 to 90 mm.

*Form.*—Uniform, symmetrical, regular, round.

*Average weight.*—200 to 220 g.

*Cavvity.*—Obtuse, shallow, depth 26 mm, width 35 mm.

*Basin.*—Symmetrical, abrupt at base, wide, depth, 12 mm, width 30 mm.

*Calyx.*—Closed, segments persistent, erect, outer and inner surfaces pubescent.

Skin:

*Thickness.*—Thin.

*Texture.*—Very smooth, glossy with medium cuticle wax.

*Tendency to crack.*—None.

*Lenicels.*—White, inconspicuous, small, few in number.

*Color.*—Solid blush 90% to 100% Red Group 59 A, with no striping.

*Ground color.*—Grayed Yellow 160 B with Yellow Green 145 A.

Flesh:

*Aroma.*—Sweet, aromatic.

*Color.*—Green White 157 B.

*Texture.*—Firm, tender, fine, crisp.

*Eating quality.*—Best.

Core:

*Bundle area.*—Medium to ovate, cordate, symmetrical at base.

*Bundle.*—Inconspicuous, green, alternate above stamens.

*Carpillary area.*—Distinct, medium size.

*Calyx tube.*—Slightly urn shaped, open.

*Depth of tube to shoulder.*—16 mm.

*Styles.*—Distinct, pubescent.

*Stamens.*—One distinct whorl, small.

*Axillary cavity.*—Wanting.

*Seed cells.*—Walls thin, tough, length 17 mm, width 6 mm.

*Longitudinal section.*—Broadly ovate.

Seeds:

*Number perfect.*—8 to 12.

*Number in one cell.*—2 to 4.

*Length.*—8 mm.

*Breadth.*—5 mm.

*Form.*—Obtuse, non-tufted.

*Color.*—Fan 4, Grayed-Orange, 178 A.

Stem:

*Length.*—30 mm.

*Width.*—2 to 4 mm.

*Color.*—Grayed Red 178 A.

Use: Processing, fresh market, dessert.

Shipping quality: Good, subject to stem puncture.

Keeping quality: Excellent, 90 to 120 days in common storage, 6 months in controlled atmosphere storage.

Tree winter hardiness: Above average for an apple variety. Tree is hardy to −20° to −35° F.

Bud winter hardiness: −15° to −20° F., depending on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus domestica,* substantially as herein shown and described.

* * * * *

FIG. 1 'B. Thome McIntosh'
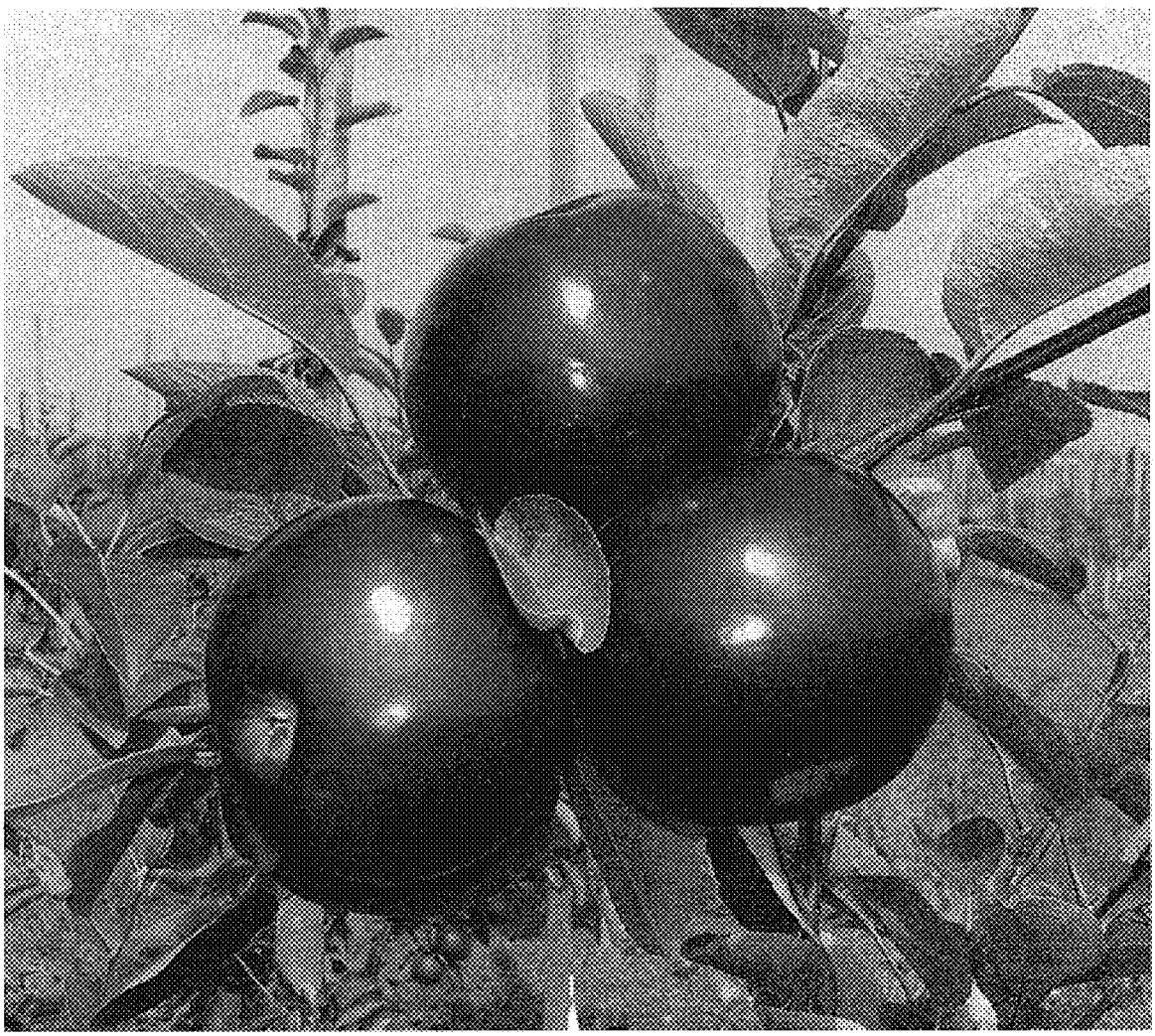

FIG. 2 'B. Thome McIntosh', Thome
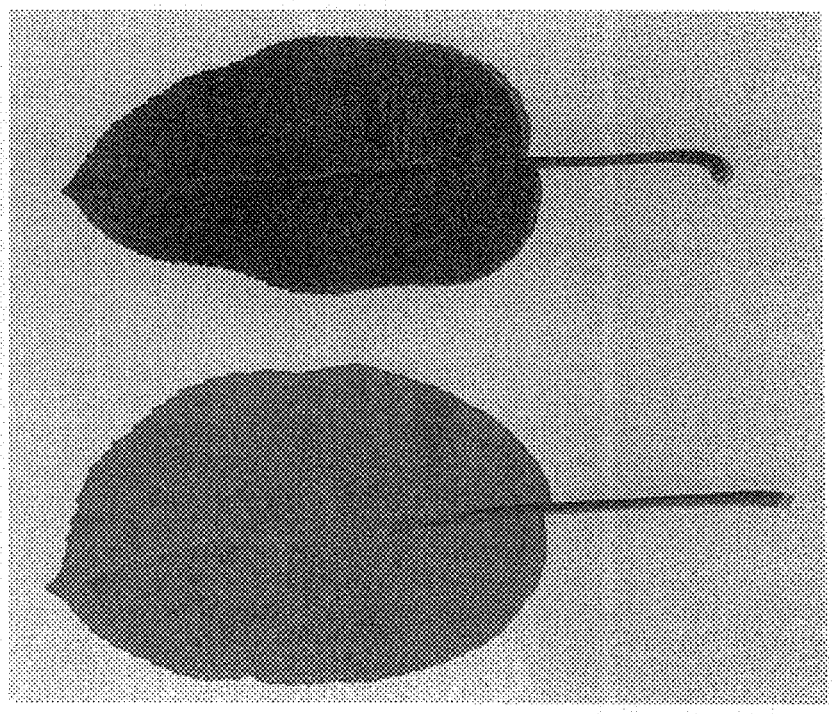
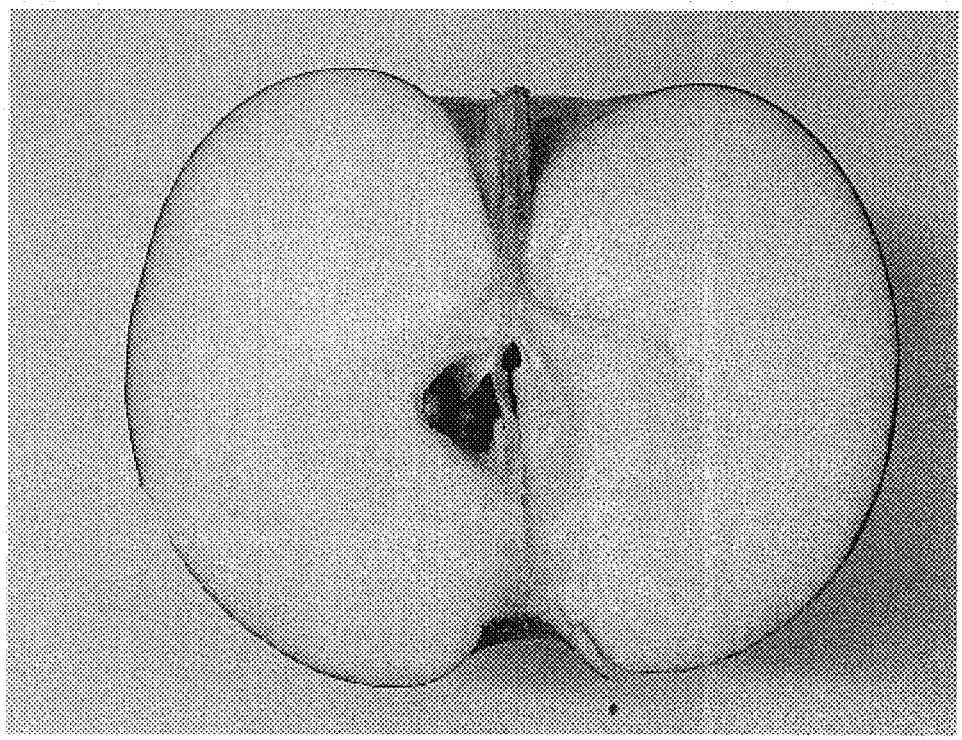

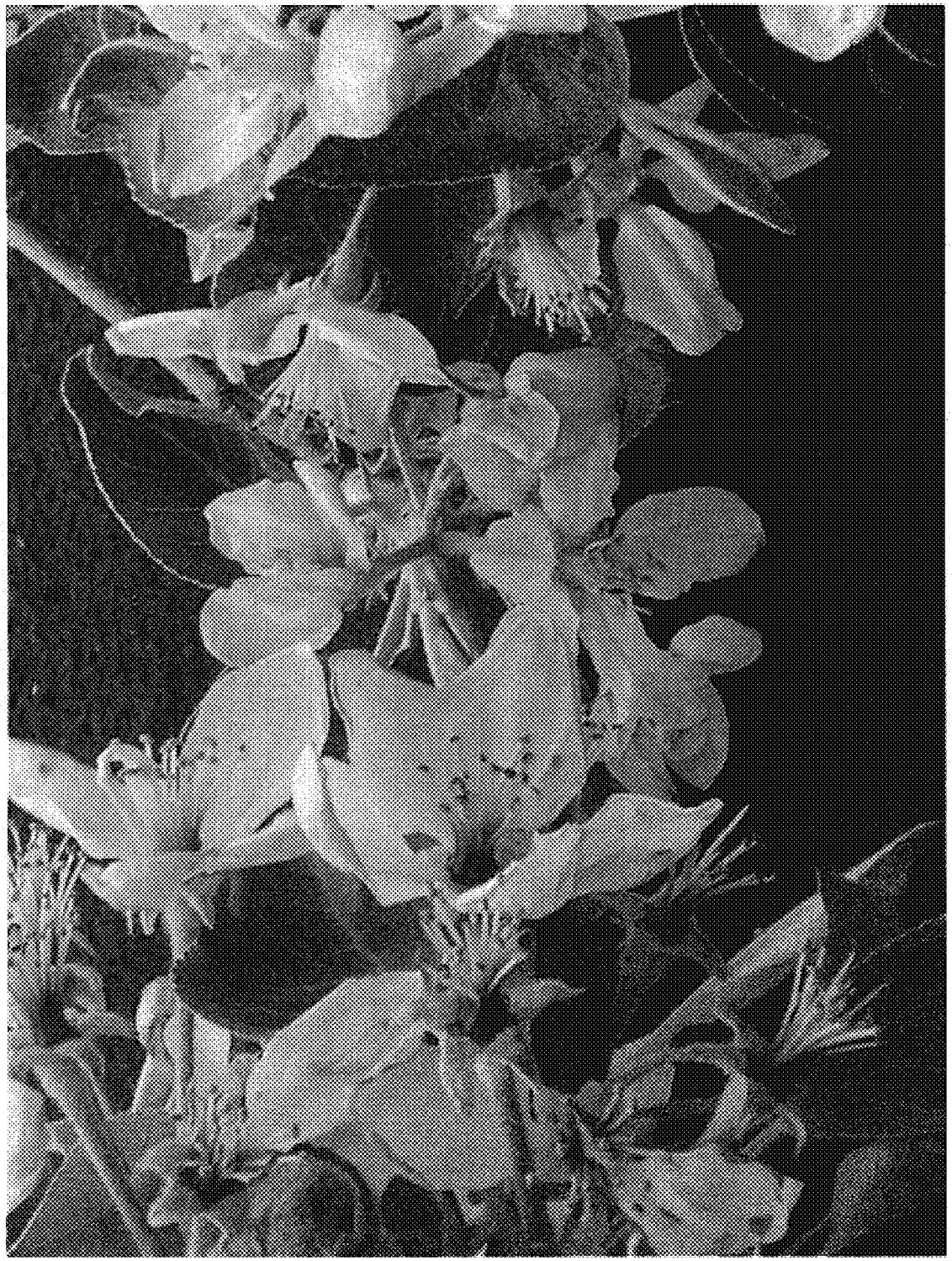

FIG. 3 'B. Thome McIntosh', Thome